United States Patent
Krueger et al.

(10) Patent No.: US 8,746,172 B2
(45) Date of Patent: Jun. 10, 2014

(54) APPARATUS AND METHOD FOR THE PLASMA TREATMENT OF HOLLOW BODIES

(75) Inventors: Jochen Krueger, Thalmassing (DE); John Felts, Alameda, CA (US)

(73) Assignee: Krones AG, Neutaubling (DE)

(*) Notice: Subject to any disclaimer, the term of this patent is extended or adjusted under 35 U.S.C. 154(b) by 831 days.

(21) Appl. No.: 12/533,747

(22) Filed: Jul. 31, 2009

(65) Prior Publication Data
US 2010/0034985 A1 Feb. 11, 2010

(30) Foreign Application Priority Data
Aug. 8, 2008 (DE) .......... 10 2008 037 159

(51) Int. Cl.
*C23C 16/50* (2006.01)
(52) U.S. Cl.
USPC ...................... 118/723 R; 118/730
(58) Field of Classification Search
CPC ................................................ H01J 37/32394
USPC .................. 118/715, 722, 723 R, 723 E, 730; 156/345.43–345.47; 315/111.21
See application file for complete search history.

(56) References Cited

U.S. PATENT DOCUMENTS

| 28,076 | A | | 5/1860 | Griswold |
|---|---|---|---|---|
| 5,308,649 | A | * | 5/1994 | Babacz .......................... 427/562 |
| 5,798,139 | A | * | 8/1998 | Nagashima et al. .......... 427/237 |
| 6,112,695 | A | | 9/2000 | Felts |
| 6,180,191 | B1 | | 1/2001 | Felts |
| 6,376,028 | B1 | * | 4/2002 | Laurent et al. ................ 427/571 |
| 6,539,890 | B1 | | 4/2003 | Felts |
| 6,561,942 | B2 | | 5/2003 | Wehking |
| 7,513,953 | B1 | * | 4/2009 | Felts ............................. 118/719 |

(Continued)

FOREIGN PATENT DOCUMENTS

| DE | 10035177 | 2/2002 |
|---|---|---|
| DE | 10202311 | 8/2003 |

(Continued)

OTHER PUBLICATIONS

German Search Report for 102008037159.9.

*Primary Examiner* — Maureen Gramaglia
(74) *Attorney, Agent, or Firm* — Marshall, Gerstein & Borun LLP

(57) ABSTRACT

The present invention refers to an apparatus for the plasma treatment of hollow bodies, comprising a vacuum treatment chamber and means for generating the plasma, which apparatus is characterized in that the means for generating the plasma comprise an electrode of a substantially U-shaped cross-section, which is arranged in the vacuum treatment chamber, the hollow bodies immersing at least in part into the U-shaped electrode when the plasma treatment is carried out, and being moved at least temporarily relative to the U-shaped electrode. Furthermore, the present invention refers to a method for the plasma treatment of hollow bodies, in which the hollow bodies are moved into a vacuum treatment chamber in which the plasma treatment is carried out and the plasma is generated by an electromagnetic field, which method is characterized in that the hollow bodies immerse at least in part into the electromagnetic field when the plasma treatment is carried out, and that the hollow bodies are moved at least temporarily relative to the electromagnetic field.

9 Claims, 3 Drawing Sheets

(56) References Cited

U.S. PATENT DOCUMENTS

| | | | |
|---|---|---|---|
| 7,854,805 B2 * | 12/2010 | Kraus et al. | 118/719 |
| 8,435,350 B2 * | 5/2013 | Humele et al. | 118/719 |
| 2002/0179603 A1 | 12/2002 | Darras et al. | |
| 2003/0159654 A1 * | 8/2003 | Arnold et al. | 118/718 |
| 2005/0227019 A1 * | 10/2005 | Hama et al. | 427/581 |
| 2008/0032059 A1 | 2/2008 | Zimmerer et al. | |

FOREIGN PATENT DOCUMENTS

| | | | |
|---|---|---|---|
| DE | 102004036063 | | 2/2006 |
| DE | 10225659 | | 1/2010 |
| JP | 05269370 A | * | 10/1993 |
| JP | 2003293155 | | 10/2003 |
| JP | 2005113202 | | 4/2005 |
| WO | WO-2007104765 | | 9/2007 |

* cited by examiner

APPARATUS AND METHOD FOR THE PLASMA TREATMENT OF HOLLOW BODIES

CROSS-REFERENCE TO RELATED APPLICATION

The present application claims the benefit of priority of German Patent Application No. 102008037159.9, filed Aug. 8, 2008. The entire text of the priority application is incorporated herein by reference in its entirety.

FIELD OF THE DISCLOSURE

The present disclosure refers to an apparatus and a method for the plasma treatment of hollow bodies. The apparatus according to the disclosure particularly serves to carry out a PECVD (plasma enhanced chemical vapor deposition) method at a reduced pressure, in which method thin layers are deposited on the inner surface of the hollow bodies.

BACKGROUND

The plasma coating of the hollow bodies particularly serves to lower the permeability of plastic bottles, particularly PET beverage bottles, with respect to gases such as oxygen and/or carbon dioxide. Conventional types of plastics have an inadequate gas barrier with respect to oxygen-sensitive and/or carbonated drinks, such as e.g. beer, juice, milk, so that the resulting shelf life of a product is too short. In comparison with uncoated reference bottles, coated PET bottles normally show a BIF (barrier improvement factor) of particularly 5 (oxygen) and about 2-3 (carbon dioxide), i.e., they have a barrier increased by this factor. This considerably prolongs the shelf life of a product.

A further application of plasma-coated PET bottles in the beverage industry is that contaminants and/or impurities inside the PET, such as acetaldehyde, are efficiently prevented from permeating through the layer and from passing into the interior of the bottle. Treated PET bottles can thus be used for beverages without natural flavor, such as particularly uncarbonated water.

A further advantage of coated hollow bodies is that cleaning agents and/or sterilizing agents, for instance $H_2O_2$ or soaps, cannot migrate into the wall of the hollow body and can thus not pass into the product after the hollow bodies have been filled. A further advantage is that organic filling materials/impurities do not migrate into the bottle wall, thereby permitting a re-use of the hollow bodies, e.g. for food packaging.

Apart from plasma coating, plasma sterilization is particularly possible for cleaning hollow bodies, particularly in the food or beverage packaging industry. Sterilization of the hollow bodies by means of plasma is carried out through the action of shortwave electromagnetic radiation in the UV range, as well as ionized and radical plasma components, on contaminants, such as harmful microorganisms. Plasma sterilization can be carried out as an alternative to plasma coating. Both methods can also be carried out in combination during treatment of a hollow body.

Apparatuses and methods for the plasma treatment of containers, particularly for the manufacture of plasma-coated plastic plasma containers for improving the gas barrier are generally known.

DE 102 25 659 A1 shows methods in which the interior of a workpiece is subjected in an evacuable individual chamber to plasma coating, wherein the plasma is generated by using microwave energy.

A further method for the inner coating of particularly PET bottles is described in US 2002/1,796,031 A1. A carbon-containing coating is here applied to the inside of the bottles via a plasma method in which the bottle to be coated is introduced into an individual chamber and a plasma is generated by means of microwave energy in the interior of the bottle.

The methods disclosed in the prior art have the drawback that the plasma treatment of the hollow bodies is carried out in individual chambers in which a respective hollow body is positioned. In the case of a large-scale implementation where a great number of coated containers are to be produced within a period of time as short as possible, this requires a great number of individual chambers of such types. As a result, such apparatuses and methods known from the prior art entail great costs and require large facility dimensions.

An approach for circumventing such drawbacks is described in DE 10 2004 03 6063 A1. Disclosed are there an apparatus and a method for plasma coating and/or sterilization in which in a vacuum chamber a plasma is generated by means of microwave energy in a vacuum chamber through a rod-shaped electrode in the interior of containers.

Microwave-generated plasmas, i.e. plasmas generated by electromagnetic waves in the GHz range, have in general the drawback that it is difficult to achieve a uniform plasma treatment of the substrates, particularly in the case of hollow bodies. This means that it is particularly difficult to guarantee the deposition of a uniform layer having a strong gas barrier. Furthermore, a high energy input is needed in the case of microwave-generated plasmas, which is disadvantageous in terms of costs.

To circumvent these drawbacks, there are proposals that the plasma should be generated by applying high-frequency energy, i.e. electromagnetic waves, in the kHz to MHz range. This is e.g. described in U.S. Pat. Nos. 6,180,191 B1, 6,539,890 B1, or 6,112,695. However, in some instances there is also described an individual chamber in which the containers are positioned during plasma treatment.

Hence, the apparatuses and methods described in the prior art are complicated, expensive or only suited to some extent for a large-scale process because they entail high costs, large dimensions and low efficiency as far as the facility is concerned.

SUMMARY OF THE DISCLOSURE

The hollow bodies of the present disclosure particularly encompass containers for packaging foodstuff, beverages or medicaments. The containers may be plastic containers of e.g. polyester, particularly PET, PS, PP or PE. Furthermore, biologically produced and/or biodegradable plastics may be used. The disclosure comprises the plasma treatment of all standard types of containers, particularly between 0.1 l and 10 l. The containers can be produced in all standard molding processes, e.g. stretch blow molding, extrusion, injection molding.

The layer may be a vitreous SiOx layer. The value of x lies, in particular, between 1.5 and 2.5. The layer is normally formed by oxidation of siloxane and/or silazane precursor molecules, particularly HMDSO, hexamethyldisiloxane, with oxygen through ionization in plasma and recombination. Oxygen is here preferably used in an excessive amount. Furthermore, carbon-containing layers, particularly so-called DLC (diamond like carbon) layers may be applied. Acetylene, in particular, is here used as the precursor molecule.

It is an aspect of the present disclosure then to provide an apparatus and a method for the plasma treatment of hollow bodies that in comparison with the conventional apparatuses and methods exhibit a compact, simplified and inexpensive design and permit a plasma treatment that is as uniform and consistent as possible.

These aspects are achieved according to the disclosure with an apparatus where there is provided a vacuum treatment chamber and means for generating the plasma, and that the means for generating the plasma comprise an electrode of a substantially U-shaped cross-section, which is arranged in the vacuum treatment chamber, the hollow bodies immersing at least in part into the U-shaped electrode when the plasma treatment is carried out, and the hollow bodies being moved at least temporarily relative to the U-shaped electrode.

The U-shaped electrode has a substantially U-shaped cross-section. The radii are freely selectable according to the disclosure. An embodiment is specifically encompassed that substantially comprises straight side walls, and the two lateral legs are arranged at a right angle relative to the bottom wall.

Alternatively, the electrode cross-section is matched to the hollow body geometry, i.e. the shape of the U-shaped electrode is substantially matched to the shape of the hollow bodies.

The U-shaped electrode is extended in longitudinal direction in the form of a tunnel. It is thereby possible to arrange a plurality of hollow bodies in the interior of the electrode at the same time. As a consequence, a plurality of separate individual chambers can be dispensed with. At the same time it is thus possible to reduce the space, i.e. the distance, between the hollow bodies. This enables a space-saving arrangement, i.e. smaller constructional dimensions.

Preferably, the U-shaped electrode is exchangeably arranged in the vacuum treatment chamber. This makes it possible to use different U-shaped electrodes for different hollow body geometries. A variable and efficient procedure and a plasma treatment of the hollow bodies that is as uniform as possible is thereby made possible because the type of U-shaped electrode can be adapted to the different geometries of the hollow bodies each time.

Size and depth of the U-shaped electrode are configured such that the space between the hollow bodies and the U-shaped electrode is as small as possible, and the hollow bodies can be introduced, if possible, entirely into the interior of the U-shaped electrode The U-shaped electrode is configured such that the majority of the conventional beverage bottles (i.e. volumes of about 0.11 to 1.01) can thereby be treated.

According to a preferred development the side walls of the U-shaped electrode are arranged in parallel with the tubular counter electrode. Particularly preferred is an arrangement in which the distance of the tubular counter electrode from the side walls of the U-shaped electrode is substantially the same. A uniform electromagnetic field can thereby be generated in the interior of the U-shaped electrode, so that the hollow bodies are plasma-treated in a way that is as uniform as possible.

The U-shaped electrode consists essentially of an electrically conductive material, particularly of copper or special steel.

According to an advantageous design of the disclosure the apparatus comprises at least two separate suction devices, one suction device generating a reduced pressure (P2) in the interior of the hollow body, and another suction device generating a reduced pressure (P1) in the interior of the vacuum treatment chamber, but outside the hollow bodies, with the pressure (P2) being smaller, preferably at least 10 to 2000 times smaller, than pressure (P1). While the plasma treatment is performed, the interior of the hollow body is sealed in gastight fashion relative to the vacuum treatment chamber. It is particularly preferred that the pressure (P2) is about 2 Pa, whereas pressure (P1) is about 3500 Pa. This guarantees that the plasma is exclusively generated in the interior of the hollow body and a plasma treatment thereby takes place exclusively in the interior of the hollow body. It is possible through the setting of the above-described pressure conditions to generate plasma in a selective way only at a place where a plasma treatment is desired. The apparatus can thereby be operated in an energetically inexpensive way. The embodiment having at least two separate pump systems further offers the advantage that the apparatus operates in a way less prone to maintenance and failure since, in comparison with apparatuses that just possess one pump system, less valves are needed for generating the different pressures (P1) and (P2).

According to a further configuration the means for generating the plasma comprise a generator for generating an electromagnetic field in the high-frequency range. Through the generation of an electromagnetic field in the high-frequency range, a plasma is generated that is very uniform in terms of intensity and expansion and thereby ensures a uniform plasma treatment of the hollow body.

The frequency range lies particularly preferably in the kHz to MHz range, particularly preferably in the range of from 1 kHz to 100 MHz. This generates a particularly uniform plasma.

Particularly in comparison with microwave plasma, high-frequency plasma can be generated in an energetically more advantageous way. A reduction of the process costs is thereby made possible. Moreover, in standard methods with microwave plasmas a multitude of individual chambers are predominantly needed for generating a uniform plasma in the interior of the hollow bodies. However, the disclosure succeeds to achieve a plasma treatment for several bottles with one single U-shaped electrode at the same time. This results in considerably reduced facility dimensions and reduced facility costs. Furthermore, the high-frequency plasmas according to the disclosure are less prone to failure, i.e. in comparison with microwave plasmas it is easier to produce a uniform plasma, i.e., the result is a particularly uniform plasma treatment.

A further embodiment of the apparatus comprises one or several tubular counter electrodes as the means for generating the plasma, the means being at least partly positioned in the interior of the hollow bodies when the plasma treatment is carried out, and the counter electrodes being provided along their longitudinal axis with a plurality of openings for introducing gases into the hollow body. Due to the tubular counter electrodes in combination with the U-shaped electrode a plasma is generated for treating the hollow bodies. The tubular counter electrode is provided with a plurality of openings along its longitudinal axis. Process gases can thereby be converted in a uniform manner in the hollow body, resulting in a particularly high uniformity of the plasma. Furthermore, one or more openings may additionally be provided on the bottom side of the tubular counter electrode. The multitude as well as the appropriate distribution of the openings across the tubular electrode has the advantage that process gases are distributed in the hollow body in a uniform and efficient way, whereby a plasma treatment that is as uniform as possible is carried out.

The openings can extend over the whole length of the tubular counter electrode and/or may be positioned at the lower end of the electrode.

It is particularly preferred that the openings in the tubular counter electrode are arranged such that the number and/or the opening diameter in the lower portion of the electrode, i.e.

in the vicinity of the container bottom, are increased. This ensures a particularly uniform plasma treatment. The diameter of the openings is preferably in the mm range, particularly in the range of 0.5 mm. The distance of the openings along the longitudinal axis is particularly within the range of about 8 mm to 25 mm. Furthermore, a plurality of openings may be provided side by side along the circumference of the tubular counter electrode.

The outer diameter of the tubular counter electrode is particularly in the mm range, preferably it is about 5 mm to 10 mm. Large diameters make the insertion of the tubular counter electrode into the hollow body difficult or even impossible, and also the suction of exhaust gases through the orifice of the hollow bodies. Small diameters have the drawback that the mechanical stability of the tubular counter electrode is inadequate.

The length of the tubular counter electrode is adapted to the height of the hollow body in the manner that there is a maximum distance of about 50 mm between the bottom of the hollow body and the lower end of the tubular counter electrode.

With larger distances a uniform plasma treatment is not guaranteed for the reason that the electromagnetic field is no longer uniform.

The tubular counter electrode is particularly designed such that the length thereof is variable and can be adapted to different lengths of the hollow bodies. This permits a variable, efficient and inexpensive design of the apparatus. A further embodiment comprises an exchangeable tubular counter electrode. Adaptation to different lengths of the hollow body can thus be carried out easily. A further advantage is the ease of exchange due to maintenance work or the like.

The tubular counter electrode consists essentially of an electrically conductive material, particularly copper or special steel, and it is connected in an electrically conductive way via the generator to the U-shaped electrode.

In a further embodiment the tubular counter electrode comprises at least one magnet in at least one portion, preferably at the end of the hollow body bottom. This enables a selective variation of the electromagnetic field, and thus of the plasma treatment. In particular, a uniform plasma can thereby be generated throughout the area of the hollow body, which guarantees a plasma treatment as efficient and uniform as possible. Furthermore, an enhanced plasma treatment of portions of the hollow bodies, particularly for instance the bottom of the hollow bodies, is possible in a selective way. To be more specific, the magnets serve to prevent or at least considerably reduce a coating of the tubular counter electrodes.

Number, type and arrangement of the magnets are not limited. The magnets may be composed of one or several individual magnets and are particularly constituted by commercially available, bar-shaped permanent magnets, preferably made of a cobalt/samarium alloy.

In an alternative embodiment of the apparatus the U-shaped electrode comprises a plurality of individual segments. Said subdivision into a plurality of individual segments has the advantage that the power needed per individual segment is reduced, which ensures a particularly efficient and economic apparatus construction. Furthermore, it is thereby possible to carry out a different plasma treatment in the individual segments, which particularly permits a variable plasma treatment.

In a further preferred embodiment of the apparatus, the vacuum treatment chamber comprises a means for controlling the unity of the plasma treatment of the hollow bodies among one another. This means is in particular an analyzing device for recording spectroscopic parameters of the plasma. It is thereby possible to control each individual hollow body.

The above-described aspects are further achieved according to the disclosure in that the hollow bodies are moved into a vacuum treatment chamber in which the plasma treatment is carried out and the plasma is generated by an electromagnetic field, wherein the method is characterized in that the hollow bodies immerse at least in part into the electromagnetic field when the plasma treatment is carried out, and are moved at least temporarily relative to the electromagnetic field.

A preferred design of the method comprises the following steps: introducing a rod-shaped counter electrode into the interior of the hollow bodies, and at least partly immersing the hollow bodies into the inner portion of a U-shaped electrode; setting an appropriate pressure in the hollow bodies and in the vacuum treatment chamber; adding one or more process gases and generating an electromagnetic field; generating a plasma in the interior of the hollow bodies in such fashion that the hollow bodies are positioned during plasma treatment at least temporarily in the inner portion of the U-shaped electrode, and the hollow bodies are moved relative to the U-shaped electrode. An efficient inexpensive procedure is made possible by way of such a procedural sequence.

In a preferred embodiment a reduced pressure (P2) is set in the interior of the hollow bodies and a reduced pressure (P1) is set in the interior of the vacuum treatment chamber, but also outside the hollow bodies, with the pressure (P2) being smaller, preferably by at least 10 to 2000 times, than the pressure (PI). This guarantees that within the method according to the disclosure the plasma treatment only takes place in the interior of the hollow bodies, which ensures a particularly efficient plasma treatment.

According to a further design of the disclosure the plasma is generated by an electromagnetic field in the high-frequency range. This permits a particularly efficient and especially uniform plasma treatment of the hollow bodies. Furthermore, the generation of a plasma by way of an electromagnetic field according to this embodiment can be carried out in a very inexpensive and efficient way.

In a further embodiment of the method, in the course of the plasma treatment an individual hollow body is treated with different plasmas that are generated due to different electromagnetic fields with respect to field strength and/or frequency. This permits a particularly efficient plasma treatment of the hollow body, and the method can be configured in a particularly flexible way.

A preferred design is characterized in that the electromagnetic field is varied by one or a plurality of magnets in the interior of the tubular counter electrode. Ions and electrons can be deflected and/or controlled by magnets. As a consequence, the electron and ion current, and thus the plasma quality inside the hollow bodies can be set through a suitable arrangement of the magnets inside the tubular electrode in such a way that a preferred plasma treatment of the hollow bodies, i.e. one that is as uniform as possible, is rendered possible. Especially in the case of a plasma coat, this prevents or at least considerably reduces a coating of the electrode.

According to a preferred variant of the method, process gases are added into the hollow bodies through one or more openings on the tubular counter electrode that are preferably positioned along the longitudinal axis, along the circumference and particularly at the lower end of the rod-shaped counter electrode. The introduction of process gases can thereby be adjusted such that a uniform plasma treatment is achieved throughout the hollow body. This permits an efficient, fast and inexpensive procedural sequence.

Due to the plasma process the tubular electrodes are heated while the plasma treatment is carried out. This offers the advantage that particularly in the case of a plasma coating no layer is deposited on the surface of the tubular counter electrode, or the layer deposition is reduced considerably. When high-frequency energy is used, the tubular counter electrode is heated without any active heating elements, or the like, because due to electrical friction losses a heating of the electrodes takes place. This must particularly be regarded as an advantage with respect to microwave-generated plasmas because the tubular counter electrode is here heated less strongly. The temperature of the tubular counter electrode during performance of the method is particularly within the range of not more than about 100° C. The advantage of such heating must particularly be seen in the fact that the openings in the tubular electrode during plasma coating are not coated or are coated less strongly, and a uniform gas input is thereby possible according to the disclosure for a long period of time. This permits an efficient and inexpensive procedure because maintenance, e.g. an exchange of the rod-shaped electrodes, is not needed or only needed to a reduced degree.

The disclosure particularly encompasses a method in which the plasma treatment is a PECVD process (plasma enhanced chemical vapor deposition) for the inside coating of the hollow bodies particularly with a SiOx layer. Such a plasma treatment reduces the gas permeability of hollow bodies, particularly of PET bottles, in an efficient and inexpensive way, so that the permeability relative to gases, for instance oxygen and/or carbon dioxide, is considerably reduced.

The layer thicknesses are particularly in the nanometer range, preferably in the range of 1 nm to 100 nm, particularly preferably in the range of 10 nm to 30 nm. It is not ensured in the case of thin layers that a uniform layer covers the surface. Thick layers have the drawback that the layer gets brittle and cracked, whereby, particularly in the deformation of the coated hollow body, the layer properties, particularly the barrier properties of the layer, are deteriorated.

The method particularly serves to form a uniform layer thickness. The minimal and maximal layer thickness is preferably 50% and 150%, respectively, of the mean layer thickness. This achieves a particularly efficient barrier to gases. In cases where the layer thickness is less uniform, the barrier action is not adequate and/or only an inefficient procedure is possible because the total layer thicknesses must be increased.

In a further preferred embodiment the method is controlled with respect to the unity of the plasma treatment of each individual hollow body. The plasma in the interior of the hollow bodies is here particularly analyzed by spectroscopy in that relevant spectroscopic parameters are recorded by an analyzing instrument. In containers with inadequate parameters a subsequent isolation of the affected hollow bodies is rendered possible according to the disclosure. To be more specific, it is also possible to adapt process parameters via a loop, thereby enabling a uniform procedure.

BRIEF DESCRIPTION OF THE DRAWINGS

The present disclosure and its advantages shall be further explained with reference to the embodiments shown in the subsequent drawings, in which.

DETAILED DESCRIPTION OF THE PREFERRED EMBODIMENT

Figure 1:
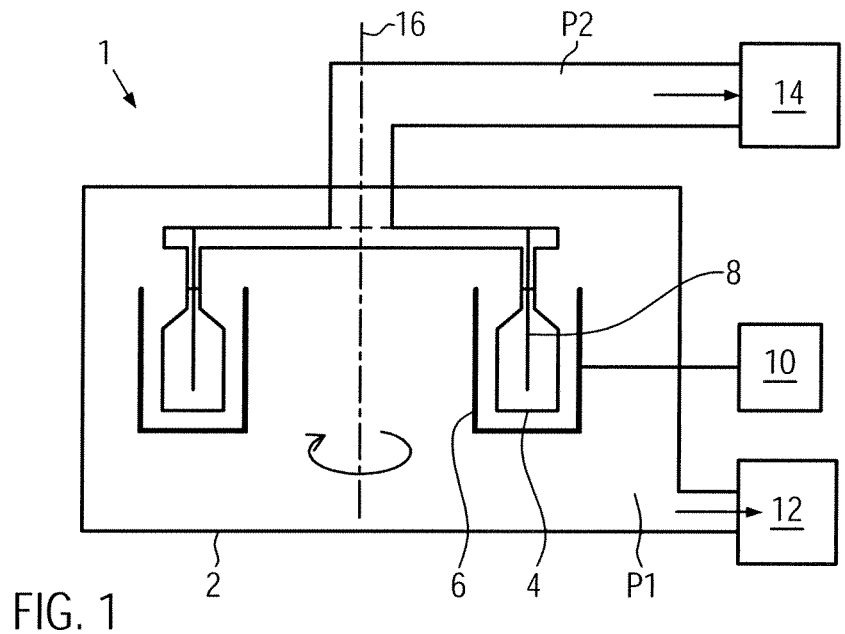
FIG. 1 is a schematic sectional drawing of an apparatus according to the disclosure.
Figure 4:
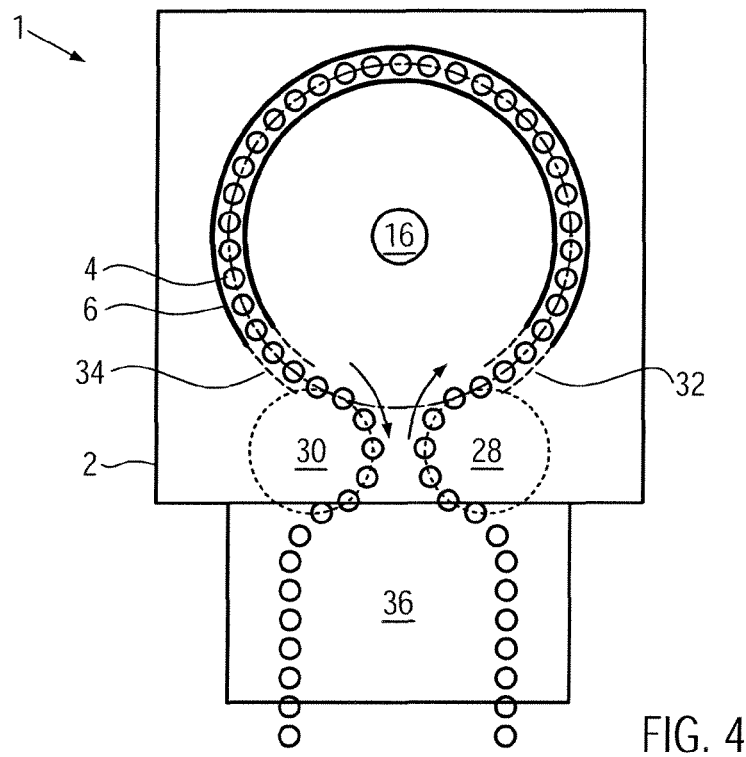
FIG. 4 is a schematic sectional top view on an apparatus according to the disclosure.

FIG. 1 schematically shows an apparatus 1 comprising a vacuum treatment chamber 2 and a U-shaped electrode 6 for accommodating the hollow bodies 4 to be treated. As can be seen in FIG. 4, the U-shaped electrode 6 extends over an angle of about 220°. The U-shaped electrode 6 is horizontally arranged along a circular path in the vacuum treatment chamber 2. The vacuum treatment chamber 2 has positioned therein a plurality of tubular counter electrodes 8 that during plasma treatment project into the interior of a respective hollow body 4. Furthermore, there is provided a means for conveying the hollow bodies 16 in the form of a rotor in the vacuum treatment chamber 2 so as to move the hollow bodies 4 relative to the U-shaped electrode 6 in such a manner that the hollow bodies 4 are moved along a circular path through the interior of the U-shaped electrode 6. The apparatus 1 comprises two separate pump systems or suction devices 12 and 14. Pump system 12 generates a vacuum (P1) in the vacuum treatment chamber 2; pump system 14 generates a vacuum (P2) in the hollow bodies 4. The pressure (P2) is at least 10 to 2000 times lower than the pressure (P1). To be more specific, pressure (P2) is about 2 Pa, and pressure (P1) about 3000 Pa. During plasma treatment a sucking out of the hollow body 4 is continuously carried out via pump system 14.

The U-shaped electrode 6 is electrically connected to the generator 10 and is electrically isolated from the housing of the treatment chamber 2. The generator 10 is arranged outside the vacuum treatment chamber and its housing is grounded. The generator can produce an electrical alternating voltage between the U-shaped electrode 6 and the also grounded tubular counter electrode 8. An electromagnetic field in the high-frequency range is thereby generated in the interior of the U-shaped electrode 6. The electromagnetic field is in the kHz to MHz range, particularly in the range of 1 kHz to 100 MHz. The generator output is e.g. 20 KW. The generator 10 may consist of a plurality of individual generators, e.g. of four generators with 5 KW each.

In the apparatus conventional holding and transporting systems can be used for holding or transporting the hollow bodies 4 (not shown). The grippers are preferably electrically isolated from the housing mass so as to prevent any plasma between the grippers and the U-shaped electrode.

Figure 2:
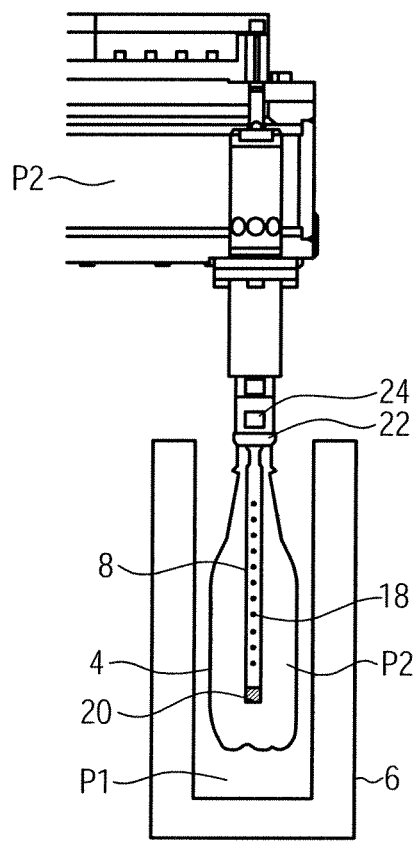
FIG. 2 is an enlarged sectional view of the apparatus with hollow bodies.

FIG. 2 shows an enlarged section of the apparatus 1, which illustrates a U-shaped electrode 6 into which a hollow body 4 is immersed. A tubular counter electrode 8 is positioned inside the hollow body 4. The hollow body 4 is sealed in gas-tight fashion relative to the interior of the vacuum treatment chamber 2 via a sealing device 22. The sealing device 22 is combined with a valve 24 which is opened during plasma treatment, so that a suction of the hollow bodies 4 by the pump system 14 to reach pressure P2 can be performed.

In an alternative embodiment, the valve connection, i.e. the valve 24 and the sealing device 22, is rotatable so that the containers 4 are rotated during coating. This permits a particularly uniform plasma treatment.

The side walls of the U-shaped electrode 6 are arranged in parallel with the tubular counter electrode 8. The distance of the tubular counter electrode 8 from the side walls of the U-shaped electrode 6 is substantially the same. As a result, a uniform electromagnetic field can be generated in the interior of the U-shaped electrode 6, so that a plasma treatment of the hollow bodies 4 that is as uniform as possible can be carried out.

Figure 3:
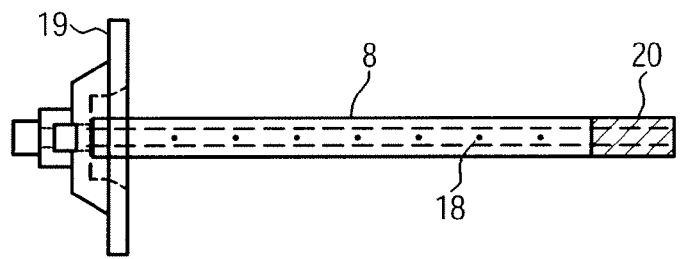
FIG. 3 is a schematic sectional drawing of the tubular counter electrode.

FIG. 3 shows in detail the design of the tubular counter electrode 8. The outer diameter of the tubular counter electrode 8 is about 10 mm. The tubular counter electrode 8 is a hollow tube and comprises a multitude of openings 18 through which the process gases can be introduced into the interior of the hollow body 4. The diameter of the openings 18 is about 0.3 mm. Along the longitudinal axis of the tubular counter electrode 8 seven openings 18 are provided; along the transverse axis four are provided at one level at an angle of 90°, so that the tubular counter electrode 8 comprises a total of 28 lateral openings 18. The distance of the openings 18 along the longitudinal axis is between about 8-25 mm. The distance of the openings 18 along the longitudinal axis is irregular in such a way that the distance between the openings towards the electrode end and the container bottom, respectively, is decreasing. In addition one or more further openings 18 are provided at the lower end of the tubular electrode 8. Due to this distribution of the openings 18 the input of process gases can be set such that a uniform plasma treatment is achieved throughout the hollow body, and an efficient, fast and inexpensive procedure is possible.

The length of the tubular counter electrode 8 is adapted to the height of the hollow body 4. The distance between the bottom of the hollow body 4 and the lower end of the tubular counter electrode 8 is not more than about 50 mm. At larger distances a uniform plasma treatment cannot be guaranteed for the reason that the electromagnetic field is no longer uniform.

The length of the tubular counter electrode 8 can be adjusted in a variable way in that the tubular counter electrode 8 is shifted relative to the sealing device 22. This permits a variable, efficient and inexpensive design of the apparatus 1 because the length of the tubular counter electrode 8 can be adapted easily and rapidly to different lengths of the hollow body 4.

Furthermore, the tubular counter electrode 8 comprises a mounting unit 19 for mounting on the sealing device 22. The mounting unit 19 is configured such that the tubular counter electrode 8 can be exchanged via a screw-type or plug-type unit in a fast and efficient way. An adaptation to different lengths of the hollow body 4 is possible through the exchange of the tubular counter electrode 8. A further advantage is the fast and simple exchangeability for reasons of maintenance.

The tubular counter electrode 8 consists essentially of an electrically conductive material, particularly copper or special steel, and it is connected in an electrically conductive way via the generator 10 to the U-shaped electrode 6.

The interior of the tubular counter electrode 8 accommodates a bar magnet (not shown) consisting of a cobalt/samarium alloy. The tubular counter electrode 8 comprises a removable sleeve 20 via which the magnet can be exchanged. The magnet extends in its length from the end of the tubular electrode up to the region in which the hollow body diameter becomes smaller. Due to the magnet the plasma is changed such that the electrode is not coated and a particularly efficient procedure is thus possible. Furthermore, a uniform plasma treatment is guaranteed.

Figure 7:
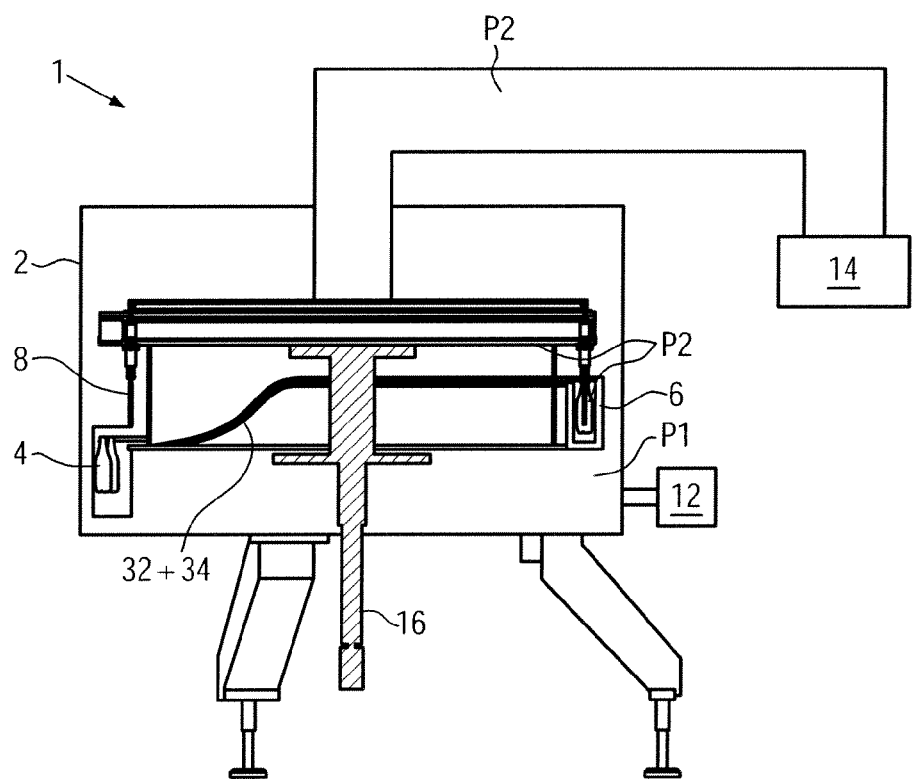
FIG. 7 is a schematic illustration of a preferred embodiment of the apparatus as a rotary apparatus.

FIG. 4 shows a design of the apparatus 1 in a top view. The apparatus 1 comprises an airlock device 36 for introducing the hollow body 4 into the vacuum treatment chamber 2. Furthermore, the apparatus 1 comprises an inlet star 30 and an outlet star 28 for the transfer of the hollow bodies 4 to a rotor 16. The rotor 16 serves to move the hollow bodies 4 relative to the U-shaped electrode 6 while the plasma treatment is carried out. The hollow bodies 4 are moved via the lifting curves 34 and 32 from the level of the inlet star 30 and outlet star 28 to the level of the U-shaped electrode 6. FIG. 7 shows the apparatus 1 once again as a sectional drawing. The hollow bodies 4 are connected to the rotor 16 via a mounting device (not shown). This is done via so-called neck handling, i.e. the mounting is carried out via the hollow body neck. Such mounting/handling systems are known from the prior art.

Figure 5:
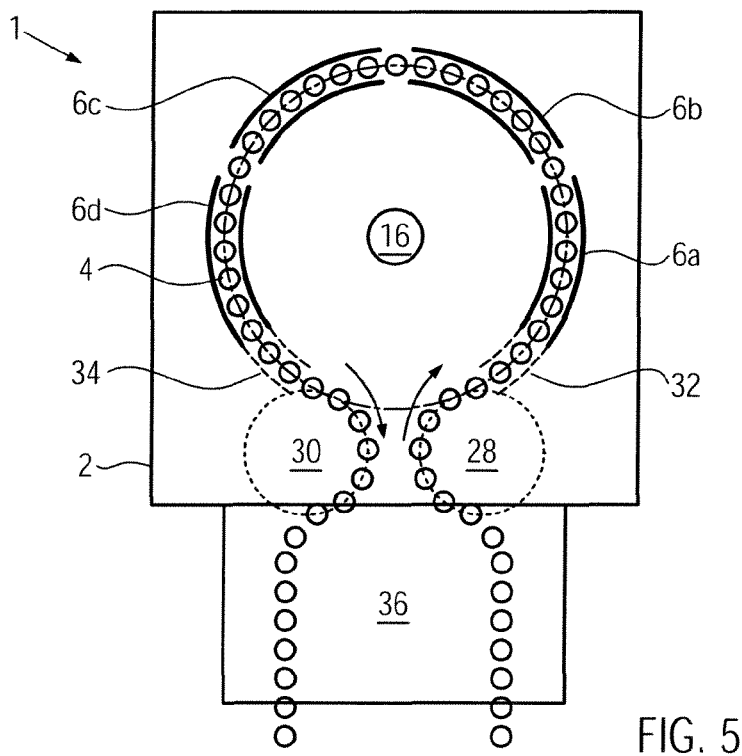
FIG. 5 is a schematic sectional drawing in the top view of a preferred embodiment of the apparatus according to the disclosure, in which the U-shaped electrode is arranged in the form of segments.

FIG. 5 shows an alternative embodiment of the apparatus 1, in which the U-shaped electrode 6 is subdivided in the form of segments, so that four segments 6a-d are formed. The presence of this U-shaped electrode 6 that is subdivided into segments has the advantage that the power needed for generating an appropriate electromagnetic field on the U-shaped electrode 6 in relation to the tubular counter electrodes 8 is reduced, so that a particularly efficient and inexpensive procedure is possible.

In the apparatus 1 a method can be carried out as follows:

A multitude of hollow bodies 4 are continuously introduced via an airlock device 36 into the vacuum treatment chamber 2 in which a vacuum (P1) is produced via the suction device 12. The hollow bodies 4 are transferred via an inlet star 30 to a rotor 16. The hollow bodies 4 are moved in a circle through the rotation of the rotor 16. Through a lifting curve 34 and with the progress of the rotary operation one hollow body each is guided over a counter electrode 8, so that the tubular counter electrode 8 is oriented into the interior of the hollow body 4.

At the same time the hollow bodies 4 are introduced at least in part into the inner portion of a U-shaped electrode 6 through the lift/rotational movement. The hollow bodies 4 are pressed against a sealing device 22 through the lifting operation, whereby a gas-tight sealing of the inner portion of the hollow body is achieved relative to the vacuum treatment chamber 2. This opens a valve 24, so that a vacuum (P2) is generated via the suction device 12 in the interior of the hollow body 4 and a continuous sucking operation is performed. Subsequently, process gases are introduced via the openings 18 of the tubular counter electrode 8 into the interior of the hollow bodies 4. The generator 10, which is connected to the U-shaped electrode 6 in an electrically conductive way, now generates an electromagnetic field relative to the grounded tubular counter electrode 8 within the inner portion of the U-shaped electrode 6. With the progressing rotation of the rotor 16 the hollow bodies 4 are moved through said electromagnetic field and a plasma is generated in the interior of the hollow bodies. This means that the plasma treatment of the hollow bodies 4 takes place while the hollow bodies 4 are positioned in the inner portion of the U-shaped electrode and are moved relative to the U-shaped electrode. After the plasma treatment a downward movement of the hollow bodies 4 is carried out via a lifting curve 32. The sealing device 22 is thereby opened and the valve 24 is closed, so that pressure (P1), which prevails in the vacuum treatment chamber 2, is set in the interior of the hollow bodies. With the progressing rotary movement the hollow bodies exit out of the inner portion of the U-shaped electrode 6, and the tubular counter electrodes 8 are removed by the downward movement out of the interior of the hollow bodies. The plasma in the interior of the treated hollow bodies 4 is thereby extinguished. Subsequently, the hollow bodies 4 are transferred from the rotor 16 to an outlet star 28 and ejected out of the vacuum treatment chamber 2.

It is possible with the method to generate plasma in a multitude of hollow bodies 4 with a single U-shaped electrode 6. Due to the presence of the electromagnetic field across the whole inner portion of the U-shaped electrode 6 an action of the plasma on each individual hollow body for a long period of time is guaranteed also during the relative movement of the hollow bodies 4. As a result, no individual chambers are needed as all of the hollow bodies positioned inside the apparatus are located in the same U-shaped electrode. This provides for a particularly efficient and inexpensive procedure because the introduction of the hollow bodies 4 into a multitude of individual chambers can be dispensed with.

The pressure is set such that pressure (P2) in the interior of the hollow bodies 4 is at least 10 to 2000 times smaller than the pressure in the vacuum treatment chamber 2 (P1). This ensures that the plasma treatment takes place exclusively in the interior of the hollow bodies 4. This has the advantage that the interior of the hollow bodies is exclusively treated. This means that the place of the plasma treatment can be controlled in an efficient way, whereby an efficient, energetically advantageous procedure is made possible.

The frequency of the electromagnetic field is in the high-frequency range, preferably in the kHz to MHz range, particularly in the range of 1 kHz to 100 MHz. This permits a particularly efficient and inexpensive procedure.

In an alternative embodiment of the procedure according to FIG. 5, a hollow body is treated with different plasmas in the course of the plasma treatment. This is achieved in that the U-shaped electrode 6a-d is built up in the form of segments, and different electromagnetic fields in terms of field strength and/or frequency are thereby generated. This has the advantage that in the course of the plasma treatment of a hollow body within the U-shaped electrode 6 the hollow body 4 passes through different electromagnetic fields due to the relative movement with respect to the U-shaped electrode 6, thereby making the plasma treatment different.

The process gases are added into the hollow body through the openings 18, which are positioned along the longitudinal axis of the tubular counter electrode 8. The simultaneous addition of the process gases via a number of openings 18 has the advantage that the process gases are added into the hollow bodies 4 in such a way that a uniform and particularly efficient plasma treatment is possible. Especially in the case of a plasma coating process a layer thickness that is as uniform as possible can thereby be achieved. This permits an efficient, fast and inexpensive procedure.

The tubular counter electrodes 8 are heated while the plasma treatment is performed. This has the advantage that particularly in the case of a plasma coating process no layer is deposited on the surface of the tubular counter electrode 8, or layer deposition is considerably reduced. The tubular counter electrode 8 is heated due to the use of high-frequency energy without active heating elements or the like because due to the plasma operation the electrodes are here heated. The temperature of the tubular counter electrode 8 is in the range of not more than 100° C. when the method is carried out. The advantage of such a heating must particularly be seen in the fact that the openings 18 are not coated or are less strongly coated during plasma coating and a uniform gas input is thereby possible according to the disclosure over a long period of time. Hence, an efficient and inexpensive procedure is possible because maintenance, i.e. an exchange of the rod-shaped electrode 8, is not needed or is only needed to a minor extent.

Figure 6:
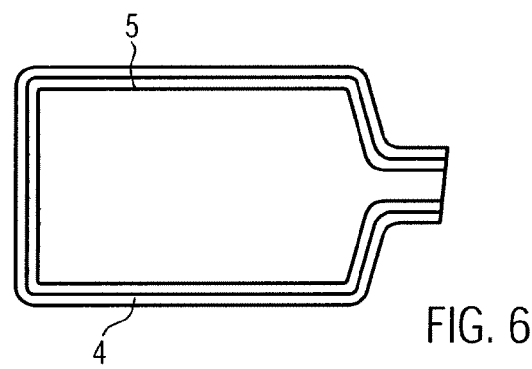
FIG. 6 is a schematic sectional drawing of a plasma-coated hollow body according to a preferred embodiment of the disclosure.

The apparatus 1 serves to carry out a plasma treatment method used for hollow bodies 4 and particularly a PECVD process for inside coating with a SiOx layer 5. Alternatively, a DLC layer may also be deposited. A coated hollow body is shown in FIG. 6.

The invention claimed is:

1. An apparatus for the plasma treatment of hollow bodies, comprising:
a vacuum treatment chamber;
means for generating the plasma, the means for generating the plasma comprising an electrode channel of a substantially U-shaped cross-section, which is arranged in the vacuum treatment chamber;
a rotary means arranged in the vacuum treatment chamber so as to move the hollow bodies relative to the U-shaped electrode channel, the hollow bodies immersing at least in part into the U-shaped electrode channel when the plasma treatment is carried out; and
at least two separate suction devices, one suction device generating a reduced first pressure in the interior of the vacuum treatment chamber, but outside the hollow bodies, and a separate suction device connected to the rotary means and generating a reduced second pressure in the interior of the hollow bodies, and the second pressure being smaller than the first pressure.

2. The apparatus according to claim 1, wherein the means for generating the plasma comprises a generator for generating an electromagnetic field in the high-frequency range.

3. The apparatus of claim 2, wherein the high frequency range is in the kHz or MHz range.

4. The apparatus according to claim 1, wherein the means for generating the plasma comprise one or more tubular counter electrodes that are positioned at least temporarily in the interior of the hollow bodies when the plasma treatment is carried out, and the tubular counter electrodes along their longitudinal axis comprising a plurality of openings for introducing gases into the hollow bodies.

5. The apparatus according to claim 4, wherein the tubular counter electrode comprises at least one magnet in at least one portion.

6. The apparatus of claim 5, wherein the at least one magnet is at the end facing the hollow body bottom.

7. The apparatus of claim 1, wherein the second pressure is at least approximately 10 to 2000 times smaller than the first pressure.

8. The apparatus according to claim 1, wherein the hollow bodies are connected to the separate suction device through sealing devices and valves provided at the rotary means.

9. The apparatus according to claim 1, wherein the separate suction device is arranged to continuously carry out a sucking out of the hollow body during plasma treatment.

* * * * *